(12) United States Patent
Cheng et al.

(10) Patent No.: US 10,213,467 B2
(45) Date of Patent: Feb. 26, 2019

(54) METHOD FOR IMPROVING MITOCHONDRIA AND METHOD FOR PROMOTING CELL DIVISION OF STEM CELL

(71) Applicant: TAIWAN MITOCHONDRION APPLIED TECHNOLOGY CO., LTD., Zhubei, Hsinchu County (TW)

(72) Inventors: Han-Chung Cheng, Zhubei (TW); Chi-Tang Tu, Zhubei (TW); Szu-Ting Liu, Zhubei (TW)

(73) Assignee: TAIWAN MITOCHONDRION APPLIED TECHNOLOGY CO., LTD., Zhubei (TW)

( * ) Notice: Subject to any disclaimer, the term of this patent is extended or adjusted under 35 U.S.C. 154(b) by 0 days.

(21) Appl. No.: 15/364,235

(22) Filed: Nov. 29, 2016

(65) Prior Publication Data

US 2017/0151297 A1    Jun. 1, 2017

(30) Foreign Application Priority Data

Nov. 30, 2015  (TW) .............................. 104139891 A

(51) Int. Cl.
*A61K 36/185* (2006.01)
*A61K 9/00* (2006.01)

(52) U.S. Cl.
CPC .......... *A61K 36/185* (2013.01); *A61K 9/0053* (2013.01)

(58) Field of Classification Search
None
See application file for complete search history.

(56) References Cited

U.S. PATENT DOCUMENTS

2012/0107432 A1* 5/2012 Antony .................. A61K 36/47
424/769

FOREIGN PATENT DOCUMENTS

| JP | 2009190988 A | 8/2009 |
| JP | 2010-178627 A | 8/2010 |
| JP | 2012-527404 A | 11/2012 |
| WO | 2013/022788 A1 | 2/2013 |

OTHER PUBLICATIONS

Antony et al. (2008) Indian Journal of Clinical Biochemistry, 23(4): 378-381. (Year: 2008).*
Chen et al. (2009) The American Journal of Chinese Medicine, vol. 37, No. 1, 19-25. (Year: 2009).*
Krishnaveni et al. (2010) J. Basic Clin. Physiol. Pharmacol. 2(1): 93-105. (Year: 2010).*
Miquel (2002) Ann. N.Y. Acad. Sci. 959: 508-516. (Year: 2002).*
Nicolson (2007) Journal of Cellular Biochemistry, 100: 1352-1369. (Year: 2007).*
Reddy et al. (2009) J. Med. Food 12(2): 327-333. (Year: 2009).*
Variya et al. (2016) Pharmacological Research, 111, 180-200. (Year: 2016).*
Mandal, et al., "Mitochondrial function controls proliferation and early differentiation potential of embryonic stem cells," HHS Public Access, vol. 29, No. 3, Mar. 2011, pp. 486-495.
JP Office Action dated Aug. 15, 2017 as received in Application No. 2016-224998 [English Translation].

* cited by examiner

*Primary Examiner* — Christopher R Tate
*Assistant Examiner* — Russell G Fiebig
(74) *Attorney, Agent, or Firm* — Maschoff Brennan

(57) ABSTRACT

The present disclosure is related to a method for improving mitochondria in a cell, comprising step of treating the cell with an extraction of *Emblica officinalis*, for improving ability of mitochondria to perform oxidative phosphorylation and synthesize adenosine triphosphate. The present disclosure is also related to a method for promoting proliferation of a stem cell, comprising step of treating the stem cell with an extraction of *Emblica officinalis*, for improving division rate of the stem cell.

8 Claims, 14 Drawing Sheets

METHOD FOR IMPROVING MITOCHONDRIA AND METHOD FOR PROMOTING CELL DIVISION OF STEM CELL

CROSS-REFERENCE TO RELATED APPLICATIONS

This non-provisional application claims priority under 35 U.S.C. § 119(a) on Patent Application No(s). 104139891 filed in Taiwan R.O.C. on Nov. 30, 2015, the entire contents of which are hereby incorporated by reference.

TECHNICAL FIELD

The present disclosure provides a method for improving mitochondria and a method for promoting cell division of a stem cell, more particularly to methods with an extraction of *Emblica officinalis*.

BACKGROUND

Mitochondria (called "mitochondrion" in singular form) are places where oxidative phosphorylation (OXPHOS) and adenosine triphosphate (ATP) synthesis occur. Since ATP is used as a source of energy in a cell, the mitochondria are described as the powerhouse of the cell. In addition to generate energy required by the cell, the mitochondria also participate in cell division, cell signaling and apoptosis of the cell, and the mitochondria has the ability to control the cell-division cycle.

SUMMARY

According to one aspect of the present disclosure, a method for improving mitochondria in a cell, comprising a step of:

treating the cell with an extraction of *Emblica officinalis*, for improving an ability of the mitochondria to perform OXPHOS and synthesize ATP.

According to another aspect of the present disclosure, a method for promoting cell division of a stem cell, comprising a step of:

treating the stem cell with an extraction of *Emblica officinalis*, for improving cell division rate of the stem cell.

BRIEF DESCRIPTION OF THE DRAWINGS

The present disclosure will become better understood from the detailed description given herein below and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Any embodiment is chosen as one exemplary reference in order to properly explain the principles of the disclosure and its practical applications, to thereby enable person skilled in the art to better utilize the disclosure. The method of the present disclosure is not limited to the specific form disclosed in one of the embodiments. Any limitation disclosed in one of the embodiments is possible to be modified or varied in view of the following teachings.

*Emblica officinalis*, also known as *Phyllanthus emblica, Emblic, Emblic myrobalan, Myrobalan, Indian gooseberry, Malacca tree*, or *Amla* from *Sanskrit amalika*, is a deciduous tree of the family Phyllanthaceae, and it is known for its edible fruit of the same name. *Emblica emblica* is native to India and distributed to South China and Malaysia.

The present disclosure discloses an extraction of *Emblica officinalis*. In some embodiments, the extraction of *Emblica officinalis* is obtained from the fruit of *Emblica officinalis* by supercritical fluid extraction, and carbon dioxide is usually used as the supercritical fluid. In some embodiments, an aqueous salt solution such as a 0.1 to 5% (w/w) of sodium chloride, potassium chloride, calcium chloride or magnesium chloride solution, methanol, ethanol, acetone and ethyl acetate is used to extract the fruit of *Emblica officinalis* to obtain an initial extract; after that, the initial extract is filtered and purified to obtain the extraction of *Emblica officinalis*.

Figure 1:
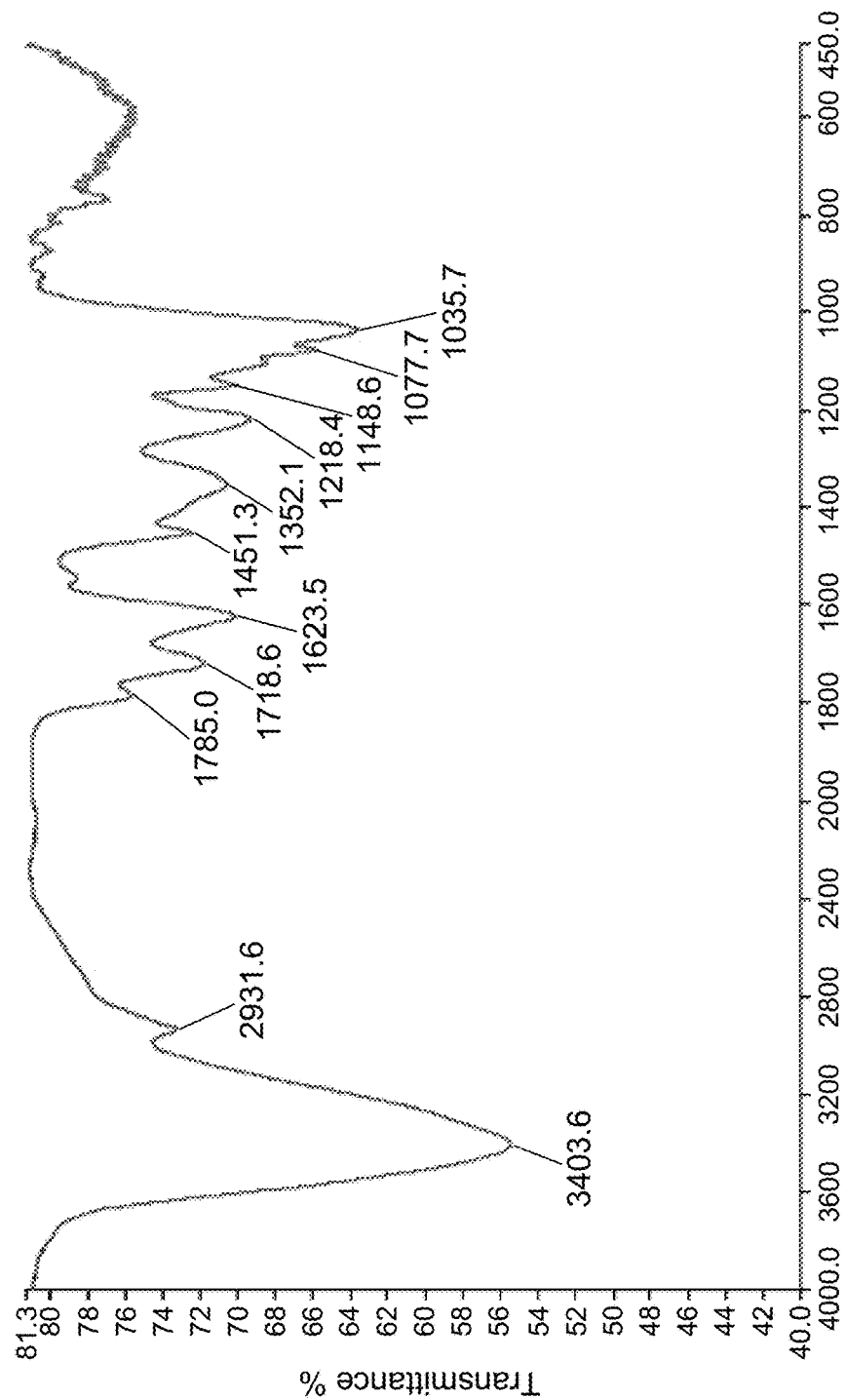
FIG. 1 is an infrared absorption spectrum of an extraction of *Emblica officinalis*.
Figure 2:
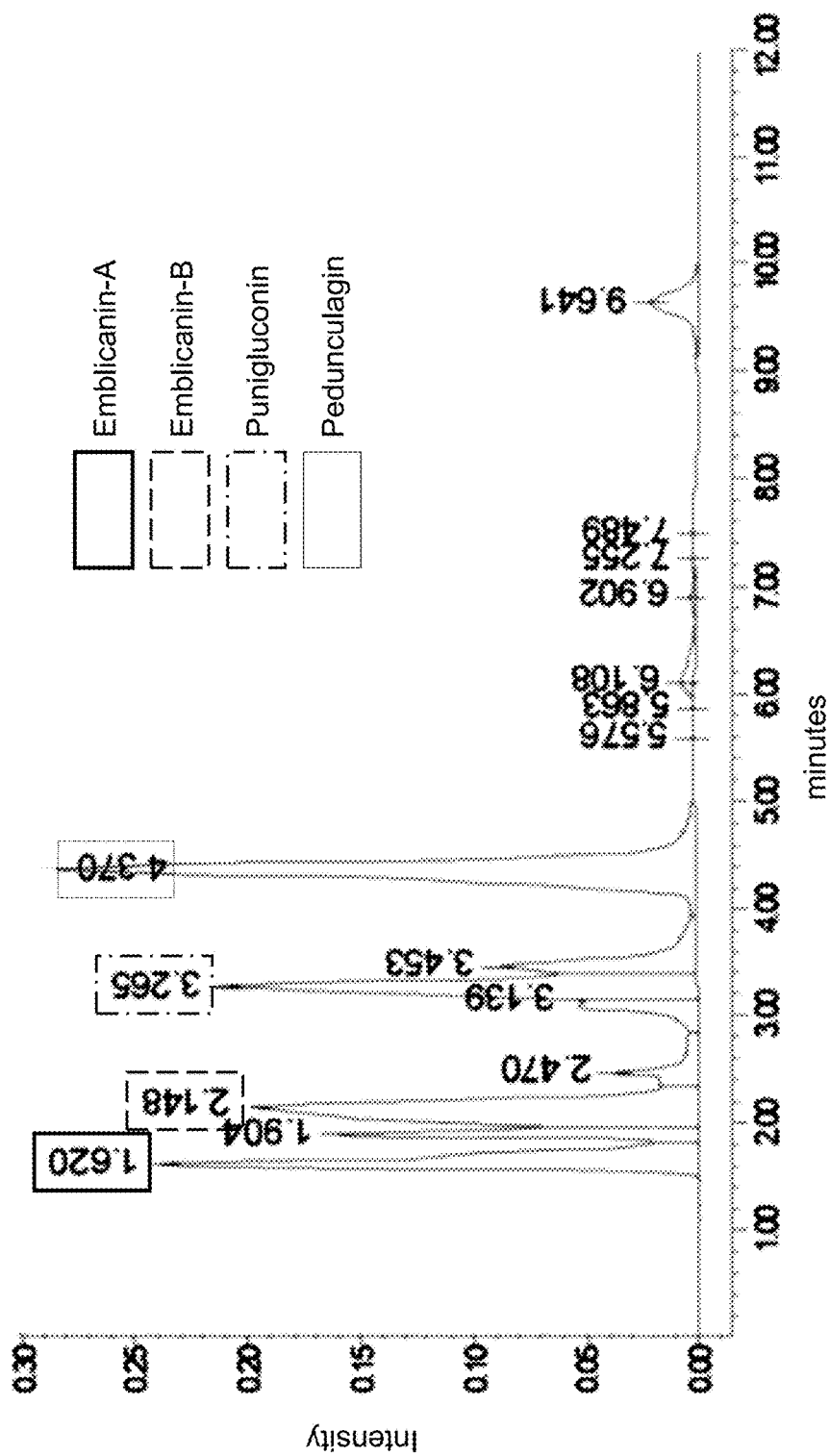
FIG. 2 is a high-performance liquid chromatogram of the extraction of *Emblica officinalis*.

In some embodiments, the extraction of *Emblica officinalis* includes 35% to 55% by weight of a mixture of Emblicanin-A and Emblicanin-B, 4% to 15% by weight of Ponigluconin, 10% to 20% by weight of Pedunculagin, 5% to 15% by weight of Rutin, and 10% to 30% by weight of Gallo-ellagitannoids. The extraction of *Emblica officinalis* has multiple characteristic infrared absorption peaks at $3403.6\pm5$ cm$^{-1}$, $2931.6\pm5$ cm$^{-1}$, $1385.0\pm5$ cm$^{-1}$, $1318.6\pm5$ cm$^{-1}$, $1623.5\pm5$ cm$^{-1}$, $1451.3\pm5$ cm$^{-1}$, $1352.1\pm5$ cm$^{-1}$, $1218.4\pm5$ cm$^{-1}$, $1148.6\pm5$ cm$^{-1}$, $1035.7\pm5$ cm$^{-1}$ and $3403.6\pm5$ cm$^{-1}$, respectively. The extraction of *Emblica officinalis* has multiple characteristic peaks on a high-performance liquid chromatogram at retention time of $1.620\pm0.5$ min, $2.148\pm0.5$ min, $3.265\pm0.5$ min and $4.370\pm0.5$ min, respectively. Please refer to FIG. 1 and FIG. 2. FIG. 1 is an infrared absorption spectrum of an extraction of *Emblica officinalis*. FIG. 2 is a high-performance liquid chromatogram of the extraction of *Emblica officinalis*.

The structural formula of Emblicanin-A, also named 2,3-di-O-galloyl-4,6-(S)-hexahydroxydiphenoyl-2-keto-glucono-lactone, is:

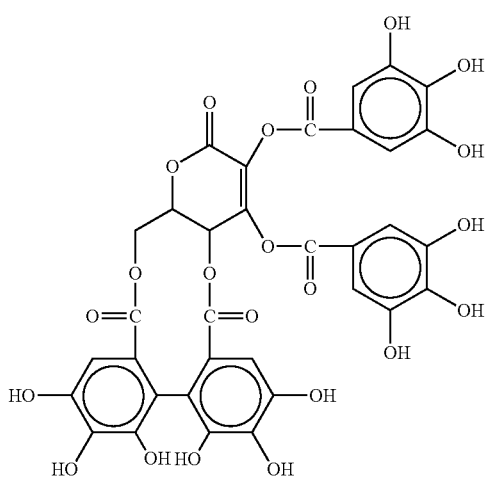

The structural formula of Emblicanin-B, also named 2,3,4,6-bis-(S)-hexahydroxydiphenoyl-2-keto-glucono-lactone, is:

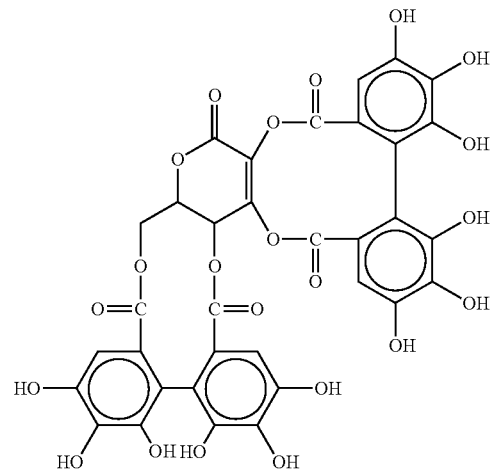

The structural formula of Ponigluconin, also named 2,3-di-O-galloyl-4,6-(S)-hexahydroxydiphenoyl gluconic acid, is:

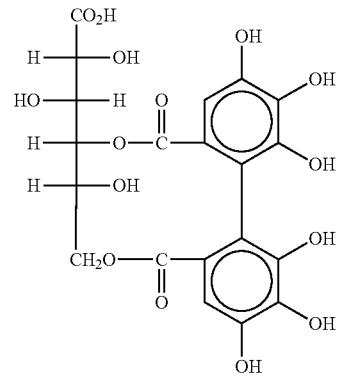

The structural formula of Pedunculagin, also named 2,3,4,6-bis-(S)-hexahydroxydiphenoyl-D-glucose, is:

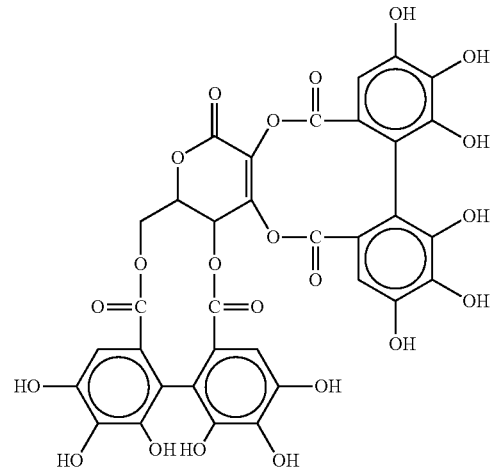

The structural formula of Rutin, also named 3',4',5,7-tetrahydroxyflavono-1,3-O-rhamnoglucoside, is:

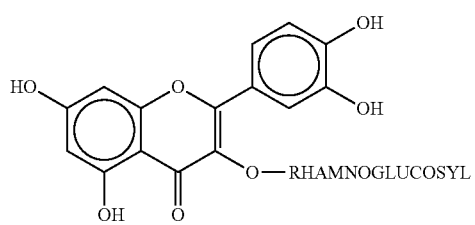

The present disclosure discloses a method for improving mitochondria in a cell, including a step of: treating the cell with the extraction of *Emblica officinalis*.

In some embodiments, the cell is treated with a composition including the extraction of *Emblica officinalis*, and a mass concentration of the extraction of *Emblica officinalis* in the composition is from 20 μg/ml to 50 μg/ml. When entering into the cell, the extraction of *Emblica officinalis* is able to protect and repair the inner membranes of the mitochondria.

Therefore, the ability of the mitochondria to synthesize ATP by OXPHOS is improved. In detail, when a mitochondrion is repaired by the extraction of *Emblica officinalis*, the yield of ATP in the mitochondrion is increased, the basal respiration in the mitochondrion during OXPHOS is increased, the proton leak at the inner membrane of the mitochondrion is decreased, the maximal respiratory capacity in the mitochondrion is increased, the spare respiratory capacity in the mitochondrion is increased, and the coupling efficiency of ATP synthesis in the mitochondrion during OXPHOS is increased.

In some embodiments, the extraction of *Emblica officinalis* is provided by oral administration; that is, a person is able to treat cells in the body by eating or drinking the extraction of *Emblica officinalis*. When the extraction of *Emblica officinalis* is provided by oral administration, the effective dose of the extraction of *Emblica officinalis* is from 216 mg to 540 mg. The effective dose in human is obtained according to a conversion equation. The conversion equation is: (effective dose in human)=(effective dose in cell experiment)×(body weight of mice)×(conversion coefficient)×(body weight of human). The conversion coefficient is obtained from the conversion coefficient table. For example, when the body weight of mice is 20 kg and the body weight of human is 60 kg, the conversion coefficient is 9.01.

When the yield of ATP synthesized by OXPHOS in the mitochondrion is increased, the energy provided for cell growth and cell division in the form of ATP is also increased, thereby improving proliferation of the cells. Accordingly, when a stem cell is treated with a composition including the extraction of *Emblica officinalis* and a mass concentration of the extraction of *Emblica officinalis* in the composition is from 50 μg/ml to 1200 μg/ml, the cell division rate of the stem cell is increased. When the mass concentration of the extraction of *Emblica officinalis* in the composition is from 50 μg/ml to 800 μg/ml, the cell division rate of the stem cell is increased more significantly.

In some embodiments, the extraction of *Emblica officinalis* is provided by oral administration to treat the stem cell. When the extraction of *Emblica officinalis* is provided by oral administration, the effective dose of the extraction of *Emblica officinalis* is from 540 mg to 12960 mg. When the effective dose of the extraction of *Emblica officinalis* is from 540 mg to 8640 mg, the cell division rate of the stem cell is increased more significantly.

To make the oral administration more convenient, the extraction of *Emblica officinalis* is able to be made into a processed food, and the processed food is able to be provided in liquid form, solid form, powder form, granular form, paste form or colloidal form. An excipient and a flavor enhancer can be added into the processed food for better flavor and convenient administration.

The excipient, for example, is wheat starch, rice starch, corn starch, potato starch, dextrin, cyclodextrin, lactose, glucose, sugar, reduced maltose, cerealose, oligofructose, galactooligosaccharide, sorbitol, erythritol, xylitol, lactitol, or mannitol. The flavor enhancer, for example, is longan extract, lychee extract, grapefruit extract, apple juice, orange juice, lemon juice, peach essence, plum essence, yogurt essence, acesulfame potassium, sucralose, erythritol, oligosaccharide, mannose, xylitol, isomerized sugar, citric acid, malic acid, tartaric acid, gluconate, green tea, oolong tea, banaba tea, eucommia tea, tieguanyin tea, coix tea, jiaogulan tea, *zizania latifolia* tea, or kelp tea.

In some embodiments, several food additives approved for use, such as colorant, preservative, tackifier, binder, disintegrant, dispersant, stabilizer, gelatinizer, antioxidant, surfactant and pH control agent, are added into the processed food of the extraction of *Emblica officinalis*.

According to the present disclosure, there are two embodiments of the present disclosure and five comparative embodiments depicted as below, for describing the method for protecting and repairing mitochondria in the cell. Several experimental data are summarized for describing the effect of the method to protect and repair mitochondria in the cell.

The following embodiments are performed by using adipose-derived stem cell (ADSC) at P6 generation. A preparation for an experimental sample is to seed a total of 8000 adipose-derived stem cells in each well of a cell culture plate, and then incubate the adipose-derived stem cells with a culture medium for 24 hours, and then remove the culture medium from the wells. A simulation of damage to the mitochondria in the adipose-derived stem cells is performed by exposing the adipose-derived stem cells to 200 mM (molar concentration) $H_2O_2$ solution for 30 minutes; and after the aforementioned exposure, the adipose-derived stem cells are washed by phosphate buffered saline (PBS).

In some experiments, a composition including the extraction of *Emblica officinalis* with predetermined mass concentration is added into the well of the cell culture plate where the stem cells are located without culture medium, and the adipose-derived stem cells in the well are incubated with the extraction of *Emblica officinalis* for 24 hours. Next, the extraction of *Emblica officinalis* is removed from the well, and 200 mM $H_2O_2$ solution is added into the well; the adipose-derived stem cells are soaked with the $H_2O_2$ solution for 30 minutes. Next, the adipose-derived stem cells are washed by PBS. Next, the oxygen consumption rate of the cell in the cell culture plate is measured by a Seahorse XF analyzer.

The Seahorse XF analyzer measures the oxygen consumption rate of the stem cells by the following steps: first, detecting the basal respiration in the stem cells; second, adding some ATP synthesis inhibitors to decrease the activity of the mitochondria to synthesize ATP, and the reduction of the oxygen consumption rate is equal to the oxygen consumption rate for ATP synthesis; third, adding some anti-couplers in a proper mass concentration, which causes no damage to the electron transport chain in the inner mitochondrial membrane, to disrupt ATP synthesis, and evaluating the maximal respiration in the mitochondria; fourth, adding some electron transport chain inhibitors to totally stop the respiration in the mitochondria, and a background value is equal to the non-mitochondrial respiration in the mitochondria.

Some parameters are obtained by the following formulas:

the basal respiration in the mitochondria=(the basal respiration in the cells)−(the non-mitochondrial respiration in the mitochondria);

the oxygen consumption rate required to compensate for free-radical leak=(the basal respiration in the mitochondria)−(the oxygen consumption rate for ATP synthesis);

the spare respiratory capacity in the mitochondria= (the maximal respiration in the mitochondria)− (the basal respiration in the mitochondria); and the coupling efficiency in the mitochondria=(the oxygen consumption rate for ATP synthesis)/ (the basal respiration in the mitochondria).

The detailed experimental data of the two embodiments of the present disclosure and the five comparative embodiments are shown in Table 1 below. The experimental data shown in Table 1 is normalized by the quantity of the stem cells.

TABLE 1

| | Mass concentration of extraction of *Emblica officinalis* in composition (μg/ml) | Oxygen consumption rate for ATP synthesis | Basal respiration in mitochondria | Oxygen consumption rate required to compensate for proton leak |
|---|---|---|---|---|
| | | | (pmol/min/μg protein) | |
| First embodiment | 50 | 20.9 | 23.1 | 2.9 |
| Second embodiment | 20 | 16.4 | 19.4 | 3.0 |
| First comparative embodiment | 0 | 12.6 | 15.8 | 4.0 |
| Second comparative embodiment | 10 | 14.4 | 18.1 | 3.8 |
| Third comparative embodiment | 75 | 10.3 | 15.9 | 5.6 |
| Fourth comparative embodiment | 100 | 9.2 | 15.2 | 6.0 |
| Fifth comparative embodiment | 150 | 11.7 | 16.8 | 5.1 |

| | Maximal respiration in mitochondria | Spare respiratory capacity in mitochondria | Non-mitochondrial respiration in mitochondria | Coupling efficiency in mitochondria |
|---|---|---|---|---|
| | (pmol/min/μg protein) | | | % |
| First embodiment | 43.2 | 20.1 | 4.5 | 87.3 |
| Second embodiment | 34.2 | 14.8 | 4.2 | 84.6 |
| First comparative embodiment | 27.4 | 12.8 | 4.0 | 77.4 |
| Second comparative embodiment | 31.7 | 13.6 | 3.5 | 79.2 |
| Third comparative embodiment | 25.6 | 13.5 | 3.8 | 64.6 |
| Fourth comparative embodiment | 24.4 | 13.2 | 4.0 | 60.8 |
| Fifth comparative embodiment | 20.6 | 7.9 | 4.1 | 70.0 |

Figure 3:
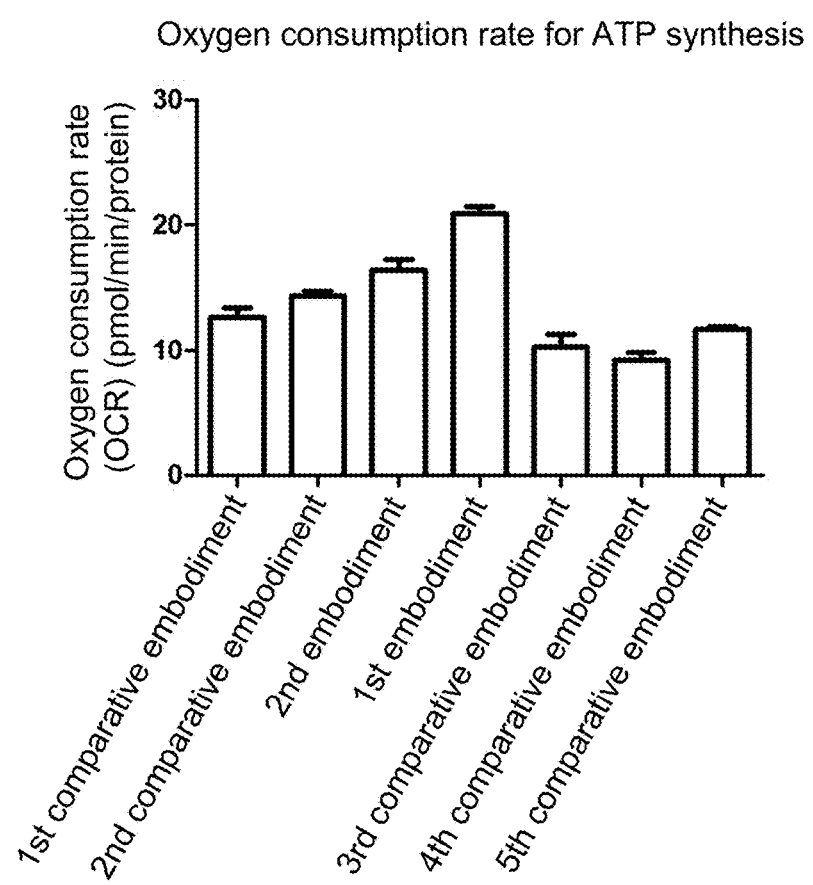
FIG. 3 is a bar chart presenting oxygen consumption rate for ATP synthesis of a first embodiment, a second embodiment, and a first through a fifth comparative embodiments.
Figure 4:
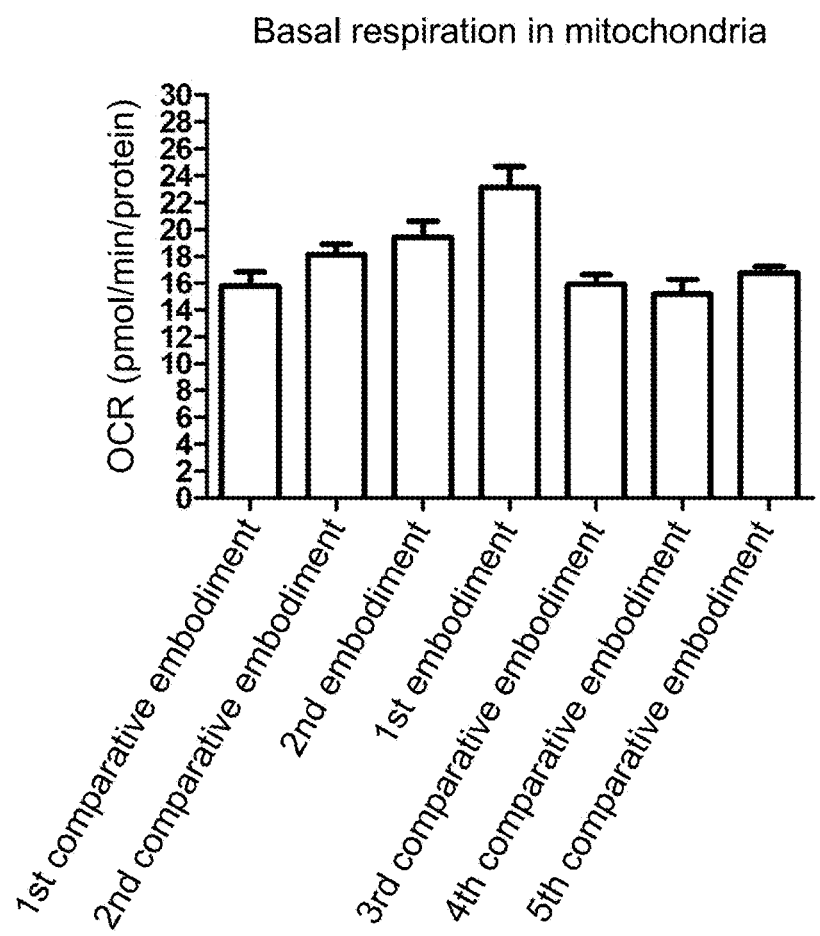
FIG. 4 is a bar chart presenting basal respiration in mitochondria of the first embodiment, the second embodiment, and the first through the fifth comparative embodiments.
Figure 5:
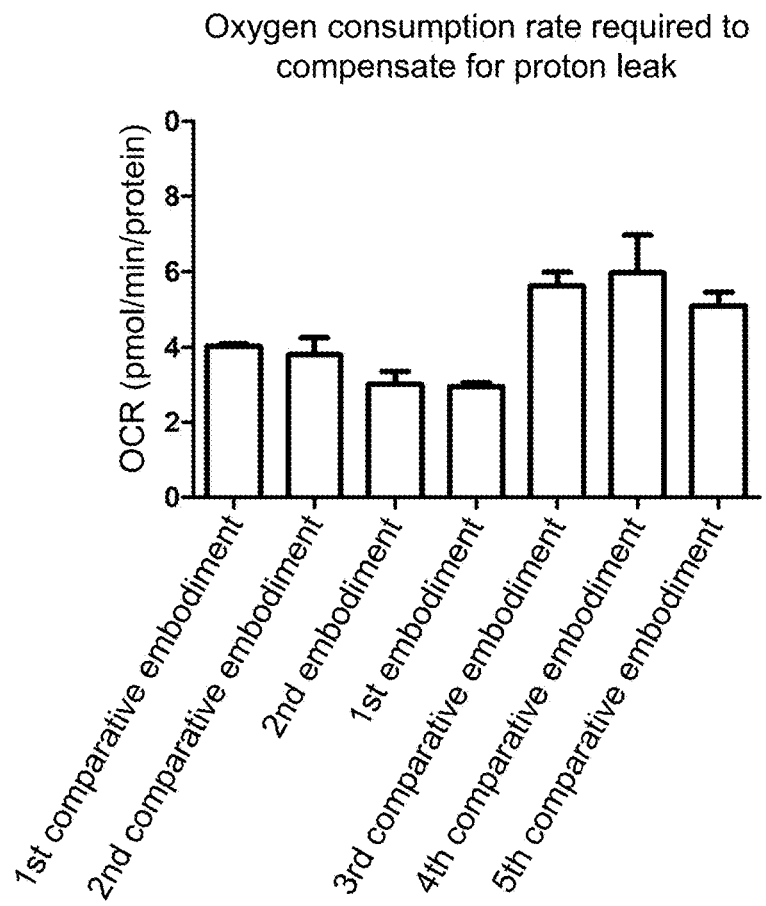
FIG. 5 is a bar chart presenting oxygen consumption rate required to compensate for free-radical leak of the first embodiment, the second embodiment, and the first through the fifth comparative embodiments.
Figure 6:
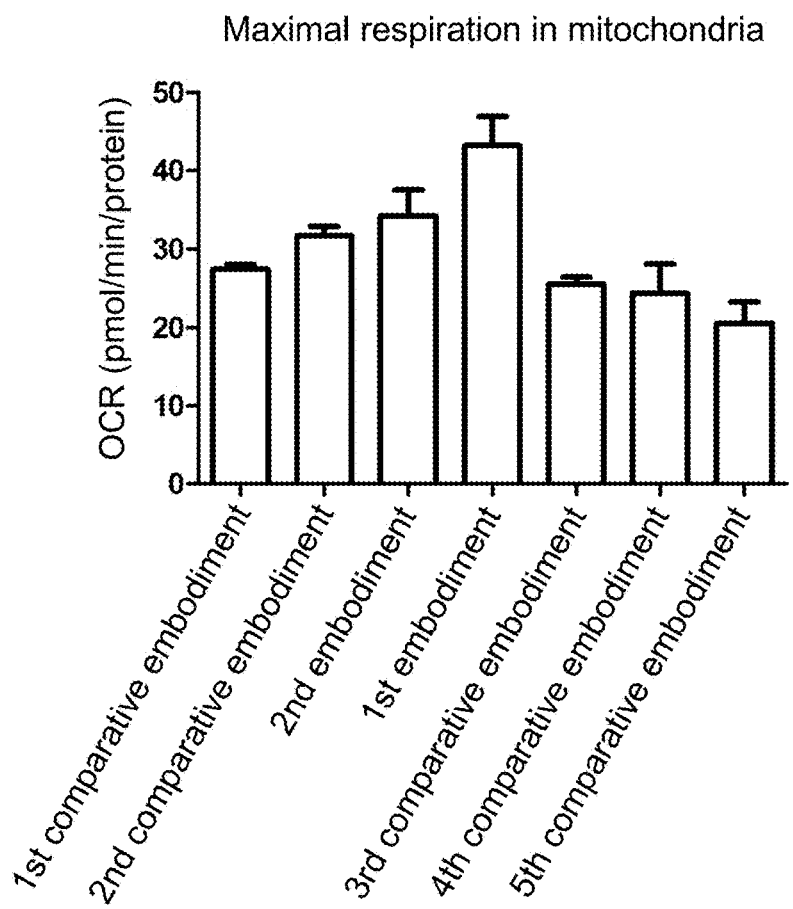
FIG. 6 is a bar chart presenting maximal respiration in mitochondria of the first embodiment, the second embodiment, and the first through the fifth comparative embodiments.
Figure 7:
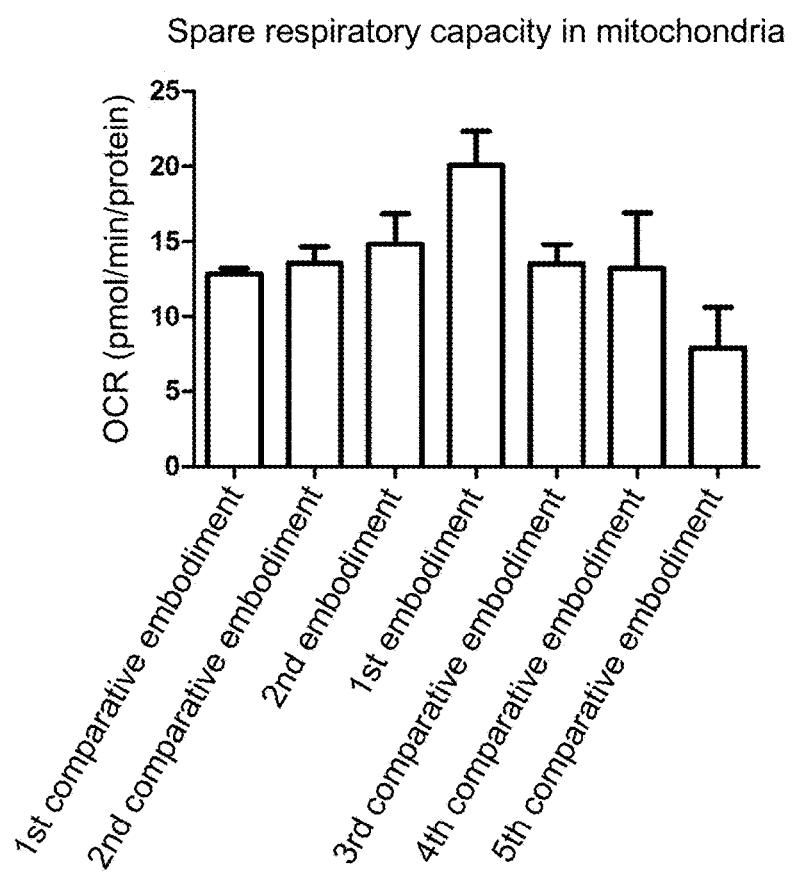
FIG. 7 is a bar chart presenting spare respiratory capacity in mitochondria of the first embodiment, the second embodiment, and the first through the fifth comparative embodiments.
Figure 8:
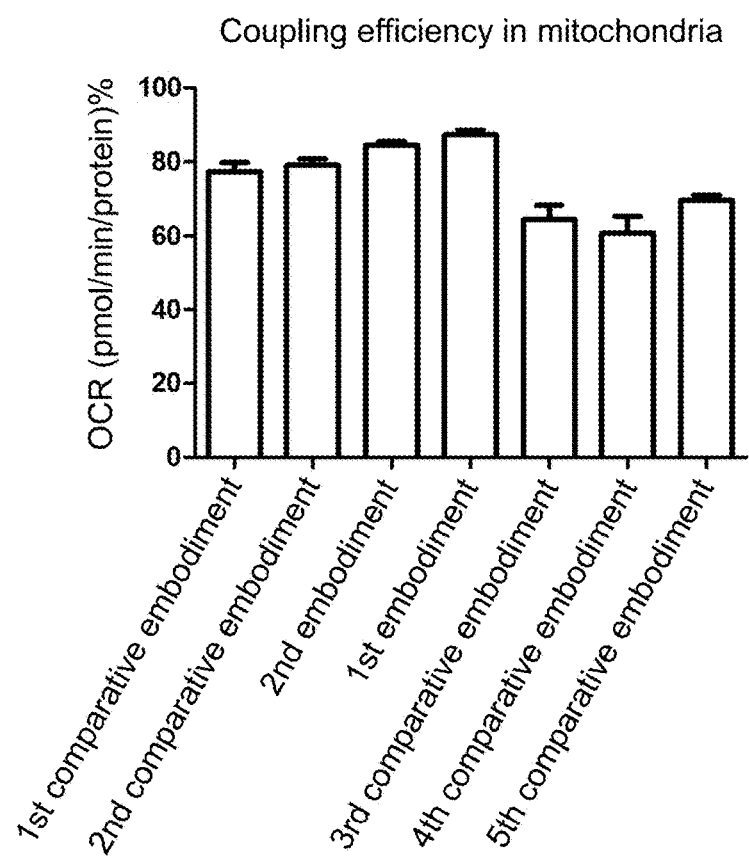
FIG. 8 is a bar chart presenting coupling efficiency in mitochondria of the first embodiment, the second embodiment, and the first through the fifth comparative embodiments.
Figure 9:
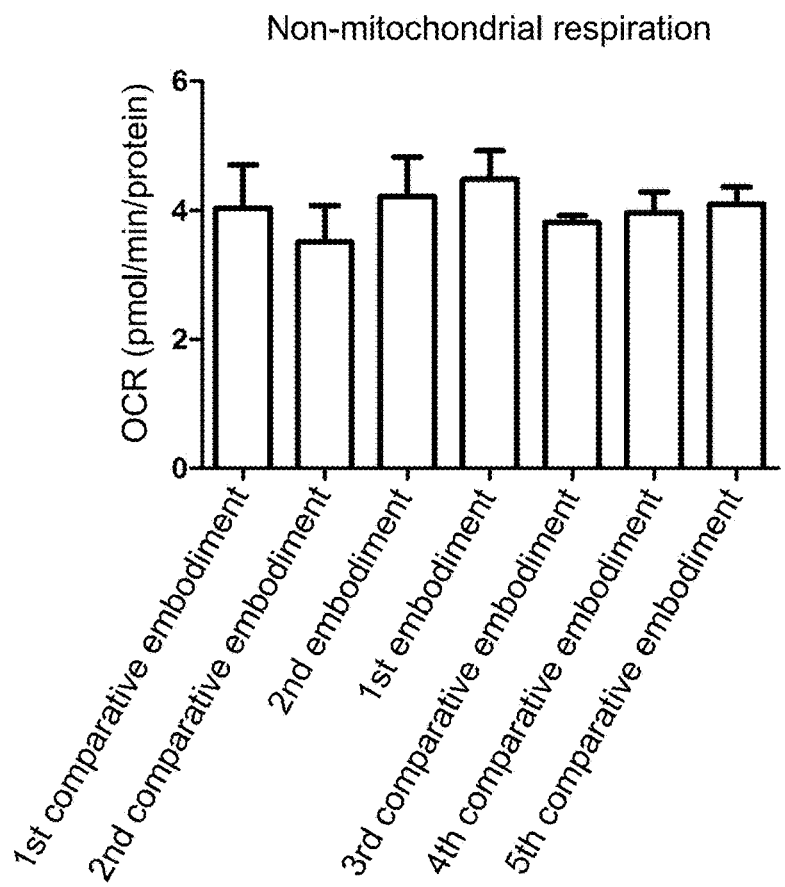
FIG. 9 is a bar chart presenting non-mitochondrial respiration of the first embodiment, the second embodiment, and the first through the fifth comparative embodiments.

Please refer to FIG. 3 to FIG. 9. FIG. 3 is a bar chart presenting oxygen consumption rate for ATP synthesis according to a first embodiment, a second embodiment, and a first through fifth comparative embodiments. FIG. 4 is a bar chart presenting basal respiration in mitochondria according to the first embodiment, the second embodiment, and the first through the fifth comparative embodiments. FIG. 5 is a bar chart presenting oxygen consumption rate required to compensate for free-radical leak according to the first embodiment, the second embodiment, and the first through the fifth comparative embodiments. FIG. 6 is a bar chart presenting maximal respiration in mitochondria according to the first embodiment, the second embodiment, and the first through the fifth comparative embodiments. FIG. 7 is a bar chart presenting spare respiratory capacity in mitochondria according to the first embodiment, the second embodiment, and the first through the fifth comparative embodiments. FIG. 8 is a bar chart presenting coupling efficiency in mitochondria according to the first embodiment, the second embodiment, and the first through the fifth comparative embodiments. FIG. 9 is a bar chart presenting non-mitochondrial respiration according to the first embodiment, the second embodiment, and the first through the fifth comparative embodiments.

As shown in FIG. 3, the oxygen consumption rate for ATP synthesis in the first and the second embodiments is larger than that in the first through the fifth comparative embodiments. As shown in FIG. 4, the basal respiration in the mitochondria in the first and the second embodiments is larger than that in the first through the fifth comparative embodiments. As shown in FIG. 5, the oxygen consumption rate required to compensate for the proton leak in the first and the second embodiments is smaller than that in the first through the fifth comparative embodiments. As shown in FIG. 6, the maximal respiration in the mitochondria in the first and the second embodiments is larger than that in the first through the fifth comparative embodiments. As shown in FIG. 7, the spare respiratory capacity in the mitochondria in the first and the second embodiments is larger than that in the first through the fifth comparative embodiments. As shown in FIG. 8, the coupling efficiency in the mitochondria in the first and the second embodiments is larger than that in the first through the fifth comparative embodiments. As shown in FIG. 9, the non-mitochondrial respiration in the mitochondria in the first and the second embodiments has no significant different from that in the first through the fifth comparative embodiments, since the extraction of *Emblica officinalis* makes influence on the oxygen consumption rate in the mitochondria while no influence on the oxygen consumption rate in the non-mitochondrial organelles.

According to the results shown in FIG. 3 to FIG. 9, in the first and the second embodiments, the basal respiration in the mitochondria is mainly used for ATP synthesis, such that the yield of ATP is increased; that is, the coupling efficiency in the mitochondria is increased. Moreover, the oxygen consumption rate required to compensate for the proton leak is decreased, such that the oxygen consumption rate for transporting protons to the intermembrane space is reduced, which indicates that the inner membranes of the mitochondria are repaired and protected by the extraction of *Emblica officinalis*.

According to the aforementioned experimental data, the mitochondria, treated with the extraction of *Emblica officinalis* having the mass concentration of 20 μg/ml to 50 μg/ml, are repaired and protected, and thereby the inner membranes of the mitochondria are prevented to be damaged by the oxidant. Also, some damaged inner membranes are repaired by the extraction of *Emblica officinalis*, such that the proton ions are prevented to leak from the intermembrane space through the inner membrane to the mitochondrial matrix; thereby, the oxygen consumption for re-transporting protons to the intermembrane space is reduced.

According to the present disclosure, there are two additional embodiment of the present disclosure and two additional comparative embodiment depicted as below, for describing the method for activating mitochondrial respiration functions. Several experimental data are summarized for describing the effect of the method to activate mitochondrial respiration functions.

The following embodiments are performed by using human fibroblast cells. A preparation for an experimental sample is to seed a total of 8000 human fibroblast cells in each well of a cell culture plate, and then incubate the human fibroblast cells with a culture medium for 24 hours, and then remove the culture medium from the wells.

In a third embodiment of the present disclosure, a total of 1 ml new culture medium and a total of 50 μg extraction of *Emblica officinalis* are added into the well of the cell culture plate, and the human fibroblast cells are incubated with the culture medium and the extraction of *Emblica officinalis* for 24 hours.

In a sixth comparative embodiment, a total of 1.0 ml new culture medium is added into the well of the cell culture plate, and the human fibroblast cells are incubated with the culture medium for 24 hours.

In a fourth embodiment of the present disclosure, a composition including the extraction of *Emblica officinalis* with a mass concentration of 50 μg/ml is added into the well of the cell culture plate where the human fibroblast cells are located without culture medium, and the human fibroblast cells are incubated with the extraction of *Emblica officinalis* for 24 hours. Next, the extraction of *Emblica officinalis* is removed from the well, and 200 mM $H_2O_2$ solution is added into the well; the human fibroblast cells are soaked with the $H_2O_2$ solution for 30 minutes. Next, the human fibroblast cells are washed by PBS.

In a seventh comparative embodiment, 200 mM $H_2O_2$ solution is added into the well; the human fibroblast cells are soaked with the $H_2O_2$ solution for 30 minutes. Next, the human fibroblast cells are washed by PBS.

The detailed experimental data of the third embodiment and the sixth comparative embodiment are shown in Table 2 below. The experimental data shown in Table 2 is normalized by the quantity of the stem cells.

TABLE 2

| | Mass concentration of extraction of *Emblica officinalis* in composition (μg/ml) | Oxygen consumption rate for ATP synthesis | Basal respiration in mitochondria | Oxygen consumption rate required to compensate for proton leak |
|---|---|---|---|---|
| | | | (pmol/min protein) | |
| Third embodiment | 50 | 21.1 | 42.7 | 22.1 |
| Sixth comparative embodiment | 0 | 17.3 | 43.8 | 27.2 |
| Fourth embodiment | 50 | 19.1 | 42.4 | 22.1 |
| Seventh comparative embodiment | 0 | 17.2 | 41.1 | 24.3 |

| | Maximal respiration in mitochondria | Spare respiratory capacity in mitochondria | Non-mitochondrial respiration in mitochondria | Coupling efficiency in mitochondria |
|---|---|---|---|---|
| | | (pmol/min protein) | | % |
| Third embodiment | 52.9 | 12.9 | 57.4 | 49.5 |
| Sixth comparative embodiment | 49.5 | 4.7 | 56.2 | 39.8 |
| Fourth embodiment | 51.5 | 11.9 | 57.4 | 49.4 |
| Seventh comparative embodiment | 32.2 | −7.5 | 58.7 | 40.6 |

Figure 10:
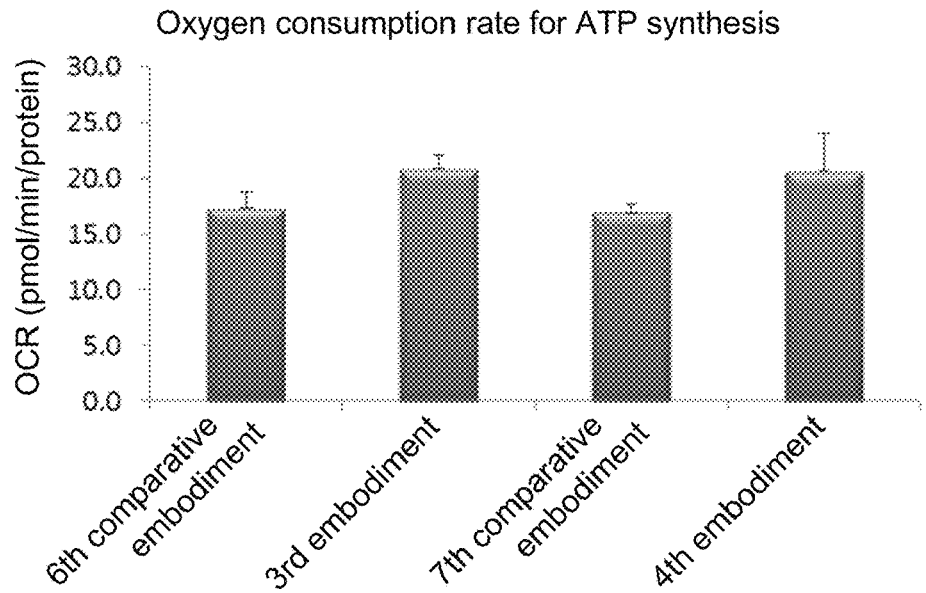
FIG. 10 is a bar chart presenting oxygen consumption rate for ATP synthesis of a third and a fourth embodiment and a sixth and a seventh comparative embodiment.
Figure 11:
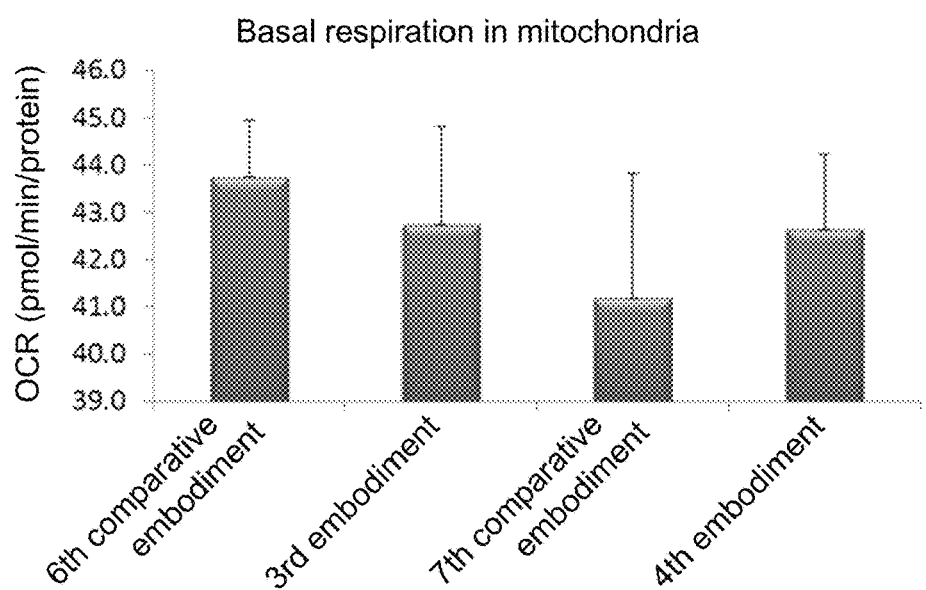
FIG. 11 is a bar chart presenting basal respiration in mitochondria of the third and the fourth embodiment and the sixth and the seventh comparative embodiment.
Figure 12:
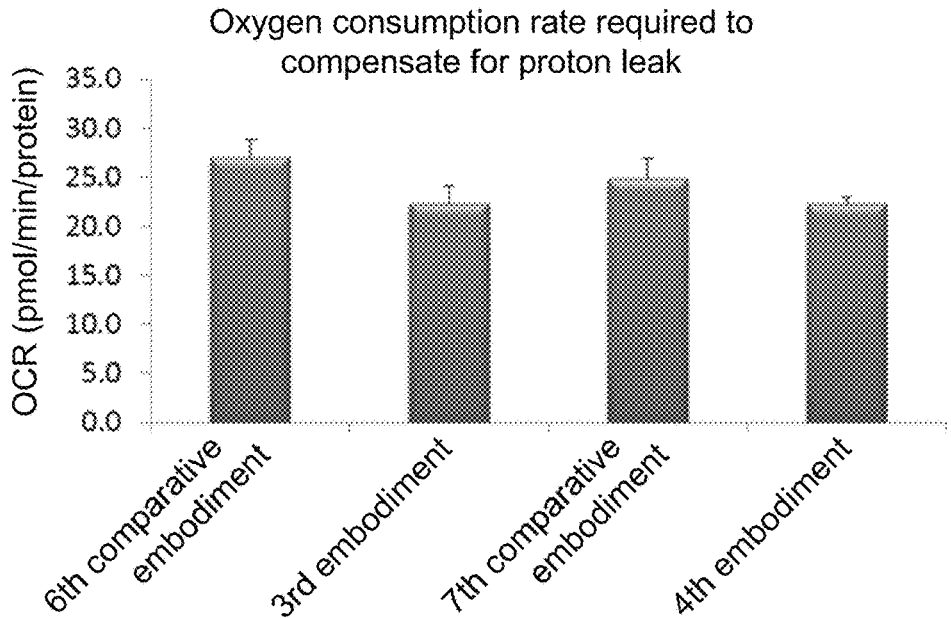
FIG. 12 is a bar chart presenting oxygen consumption rate required to compensate for free-radical leak of the third and the fourth embodiment and the sixth and the seventh comparative embodiment.
Figure 13:
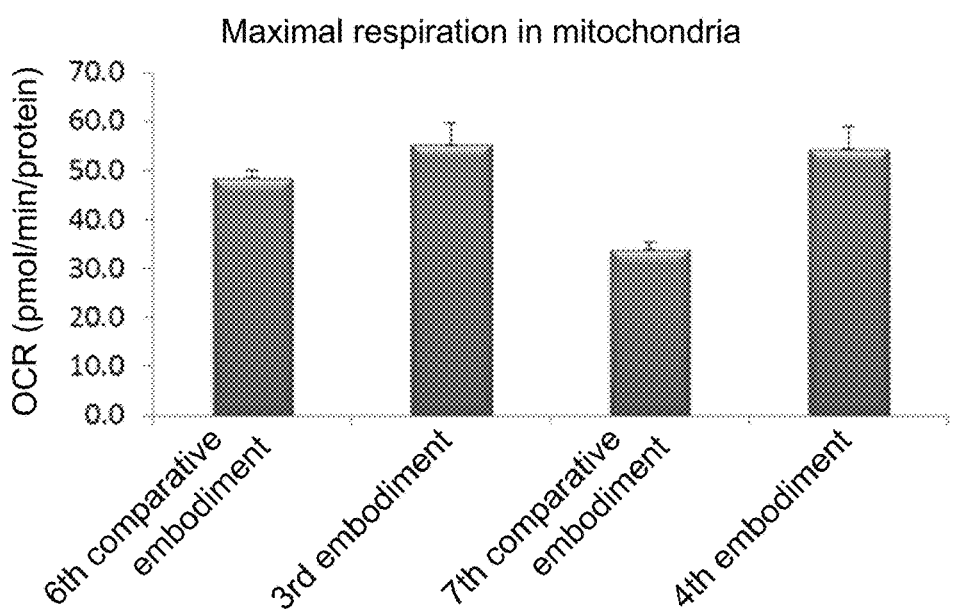
FIG. 13 is a bar chart presenting maximal respiration in mitochondria of the third and the fourth embodiment and the sixth and the seventh comparative embodiment.
Figure 14:
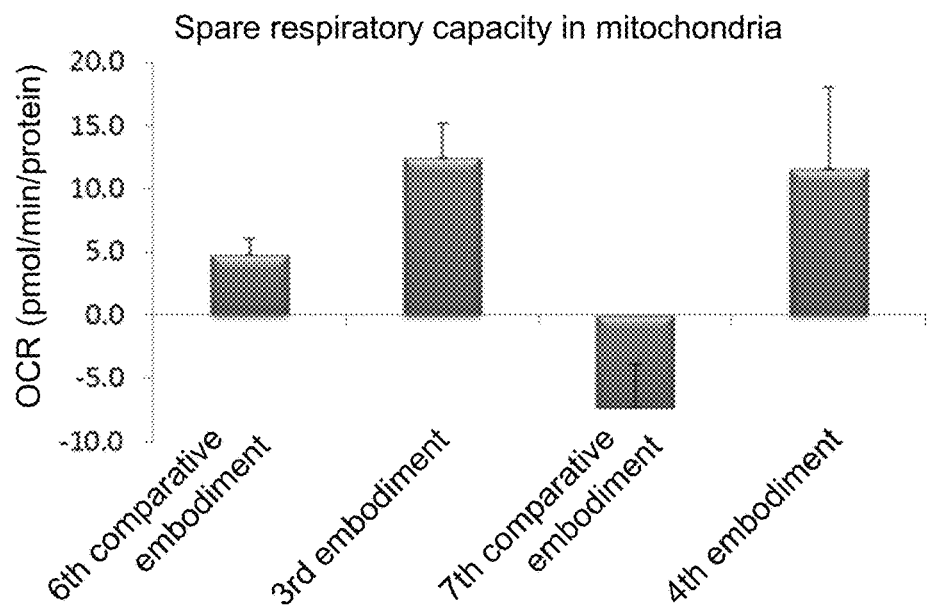
FIG. 14 is a bar chart presenting spare respiratory capacity in mitochondria of the third and the fourth embodiment and the sixth and the seventh comparative embodiment.
Figure 15:
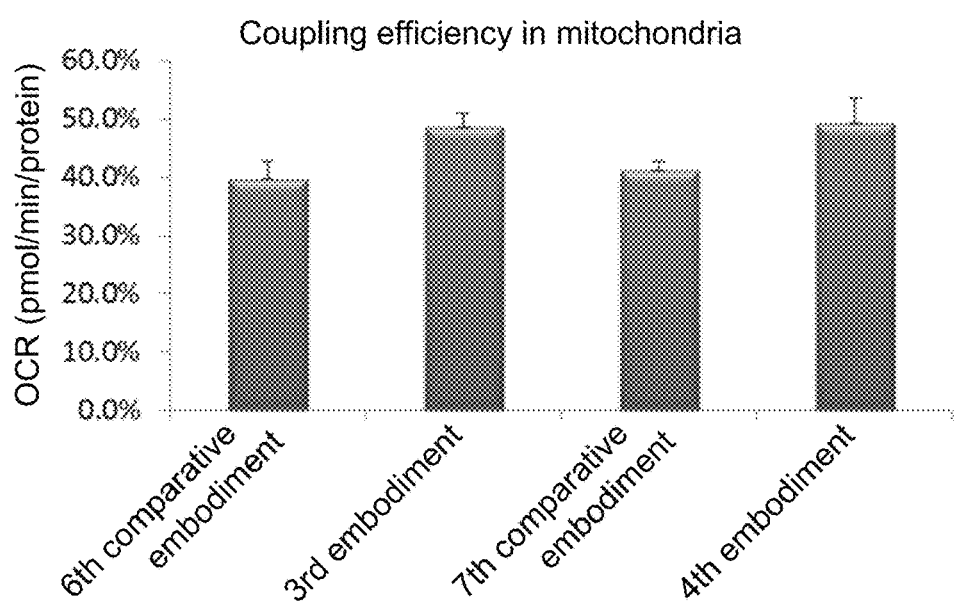
FIG. 15 is a bar chart presenting coupling efficiency in mitochondria of the third and the fourth embodiment and the sixth and the seventh comparative embodiment.
Figure 16:
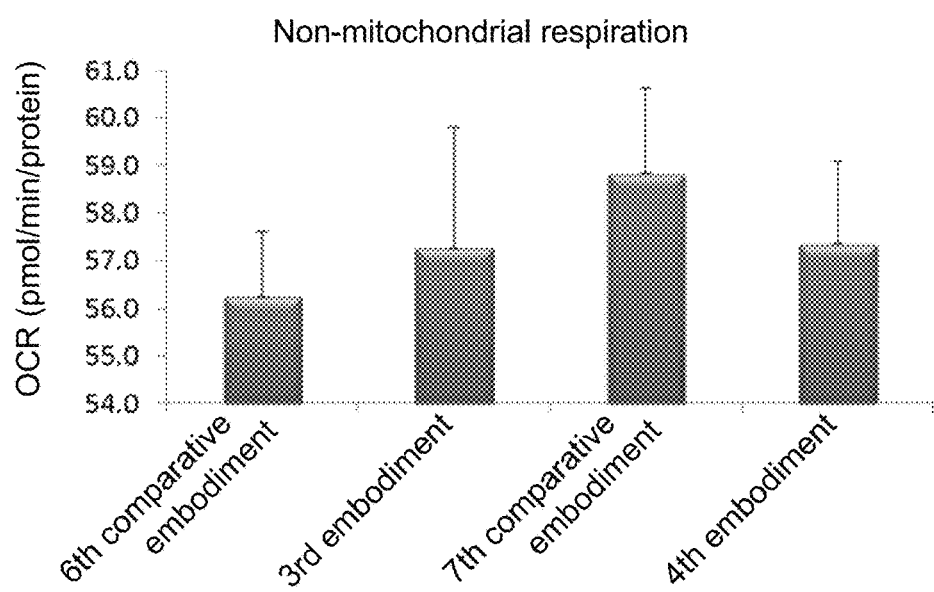
FIG. 16 is a bar chart presenting non-mitochondrial respiration of the third and the fourth embodiment and the sixth and the seventh comparative embodiment.

Please refer to FIG. 10 to FIG. 16. FIG. 10 is a bar chart presenting oxygen consumption rate for ATP synthesis according to a third and a fourth embodiment and a sixth and a seventh comparative embodiment. FIG. 11 is a bar chart presenting basal respiration in mitochondria according to the third and the fourth embodiment and the sixth and the seventh comparative embodiment. FIG. 12 is a bar chart presenting oxygen consumption rate required to compensate for free-radical leak according to the third and the fourth embodiment and the sixth and the seventh comparative embodiment. FIG. 13 is a bar chart presenting maximal respiration in mitochondria according to the third and the fourth embodiment and the sixth and the seventh comparative embodiment. FIG. 14 is a bar chart presenting spare respiratory capacity in mitochondria according to the third and the fourth embodiment and the sixth and the seventh comparative embodiment. FIG. 15 is a bar chart presenting coupling efficiency in mitochondria according to the third and the fourth embodiment and the sixth and the seventh comparative embodiment. FIG. 16 is a bar chart presenting non-mitochondrial respiration according to the third and the fourth embodiment and the sixth and the seventh comparative embodiment.

According to the results shown in FIG. 10 to FIG. 16, in the third embodiment, the inner membranes of the mitochondria are protected by the extraction *of Emblica officinalis*. Accordingly, the mitochondria, treated with the extraction of *Emblica officinalis* having the mass concentration of 50 μg/ml, are protected to inhibit the breakdown of the mitochondria, thereby improving the respiration of the human fibroblast cells to activate mitochondrial respiration functions. Furthermore in the fourth embodiment, the inner membranes of the mitochondria are protected by the extraction of *Emblica officinalis*, such that the mitochondria are prevented to be damaged by the $H_2O_2$ solution. As shown in FIG. 10 to FIG. 16, the fourth embodiment shows better oxygen consumption rate for ATP synthesis, basal respiration in mitochondria, oxygen consumption rate required to compensate for proton leak, maximal respiration in mitochondria, respiratory capacity in mitochondria, coupling efficiency in mitochondria and non-mitochondrial respiration than the seventh comparative embodiment.

According to the present disclosure, there are eight additional embodiments of the present disclosure and two additional comparative embodiments depicted as below, for describing the method for promoting cell division of a stem cell. Several experimental data are summarized for describing the effect of the method to promote cell division.

The following embodiments are performed by using ADSC at P6 generation. A preparation for an experimental sample is to seed a total of 2000 adipose-derived stem cells in each well of a cell culture plate, and then incubate the adipose-derived stem cells with a culture medium for 24 hours, and then remove the culture medium from the wells.

In some experiments, a composition including the extraction of *Emblica officinalis* with predetermined mass concentration is added into the well of the cell culture plate where the stem cells are located without culture medium, and the stem cells in the well are incubated with the extraction of *Emblica officinalis* for 24 hours. Next, a medium including 10% (v/v) Alamar Blue is added into the wells, and the stem cells are incubated with the medium including Alamar Blue for 4 hours. A reduced form of nicotinamide adenine dinucleotide (NADH) in the mitochondria of the stem cells converts Alamar Blue reagent into a detectable pink fluorescent product, and the fluorescence intensity is measured to determine the quantity of stem cells in the well.

The detailed experimental data of the eight embodiments of the present disclosure and the two comparative embodiments are shown in Table 3 below.

TABLE 3

| | Mass concentration of extraction of *Emblica officinalis* in composition (μg/ml) |
|---|---|
| Fifth embodiment | 50 |
| Sixth embodiment | 100 |
| Seventh embodiment | 200 |
| Eighth embodiment | 400 |
| Ninth embodiment | 600 |
| Tenth embodiment | 800 |
| Eleventh embodiment | 1000 |
| Twelfth embodiment | 1200 |
| Eighth comparative embodiment | 0 |
| Ninth comparative embodiment | 1400 |

Figure 17:
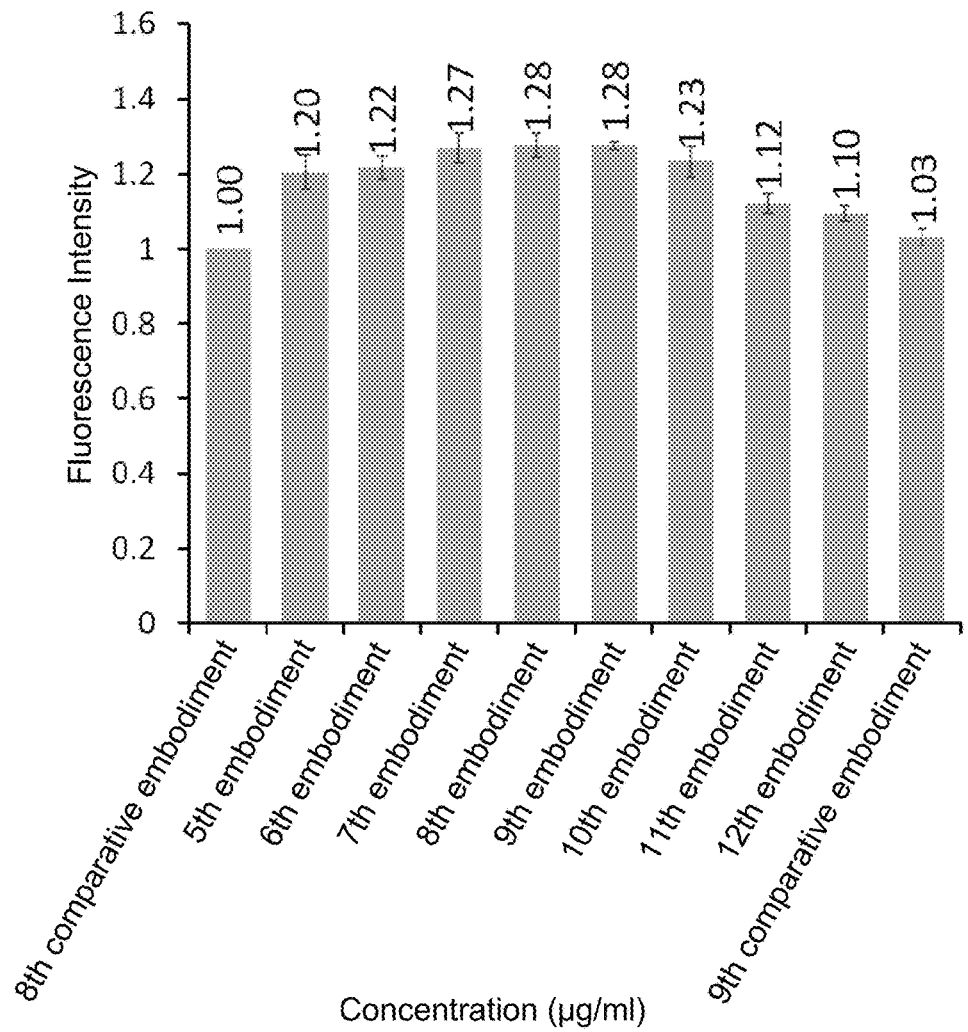
FIG. 17 is a bar chart presenting fluorescence intensity from stem cell of a fifth through a twelfth eleventh embodiments, and an eighth and a ninth comparative embodiments.

FIG. 17 is a bar chart presenting fluorescence intensity from stem cell of a fifth through a twelfth eleventh embodiments, and an eighth and a ninth comparative embodiments. As shown in FIG. 17, take the fluorescence intensity in the eighth comparative embodiment as a baseline value, the fluorescence intensity in the fifth embodiment is about 1.20 times larger than that in the eighth comparative embodiment; the fluorescence intensity in the sixth embodiment is about 1.22 times larger than that in the eighth comparative embodiment; the fluorescence intensity in the seventh embodiment is about 1.27 times larger than that in the eighth comparative embodiment; the fluorescence intensity in the eighth embodiment is about 1.28 times larger than that in the eighth comparative embodiment; the fluorescence intensity in the ninth embodiment is about 1.28 times larger than that in the eighth comparative embodiment; the fluorescence intensity in the tenth embodiment is about 1.23 times larger than that in the eighth comparative embodiment; the fluorescence intensity in the eleventh embodiment is about 1.12 times larger than that in the eighth comparative embodiment; and the fluorescence intensity in the twelfth embodiment is about 1.10 times larger than that in the eighth comparative embodiment. Stronger fluorescence intensity indicates that more amount of Alamar Blue is converted to the pink fluorescent product by the enzyme in the mitochondria of the stem cells, such that it is indicated that there are more stem cells in the well of the cell culture plate. According to the result shown in FIG. 9, the stem cell, treated with the extraction of *Emblica officinalis* having the mass concentration of 50 μg/ml to 1200 μg/ml, has higher cell division rate, such that the cell numbers in the well is increased. When the stem cell is treated with the extraction of *Emblica officinalis* having the mass concentration of 50 μg/ml to 800 μg/ml, the promotion of cell division is better.

According to the present disclosure, the cell is treated with the extraction of *Emblica officinalis* to improve the ability of the mitochondria to perform OXPHOS and synthesize ATP. In detail, the extraction of *Emblica officinalis* is favorable for protecting and repairing the inner membranes of the mitochondria. Therefore, it is favorable for preventing apoptosis of the cell due to breakdown of the mitochondria by exposing to the oxidant. Also, the extraction of *Emblica officinalis* is favorable for activating mitochondrial respiration functions, such as ATP synthesis, SRC, maximal respiration, compensation for proton leak and coupling efficiency. Furthermore, the stem cell is treated with the extraction of *Emblica officinalis* to promote cell division. Therefore, it is favorable for obtaining more stems cells having high differentiation potency for replacing damaged or old cells.

What is claimed is:

1. A method for improving the ability of mitochondria to perform oxidative phosphorylation (OXPHOS) and adenosine triphosphate (ATP) synthesis in the cells of a subject in need thereof, the method comprising:
    administering to said subject an effective amount of a composition containing an *Emblica officinalis* extract,
    wherein the concentration of the *Emblica officinalis* extract in the composition is from 20 μg/ml to 50 μg/ml; and
    wherein the *Emblica officinalis* extract comprises 35% to 55% by weight of a mixture of Emblicanin-A and Emblicanin-B, 4% to 15% by weight of Ponigluconin, 10% to 20% by weight of Pedunculagin, 5% to 15% by weight of Rutin and 10% to 30% by weight of Galloellagitannoids.

2. The method according to claim 1, wherein said administering is by oral administration.

3. The method according to claim 2, wherein the effective amount of the composition is from 216 to 540 mg.

4. The method according to claim 1, wherein spare respiratory capacity in the mitochondria is increased.

5. The method according to claim 1, wherein basal respiration in the mitochondria during OXPHOS is increased.

6. The method according to claim 1, wherein coupling efficiency in the mitochondria during OXPHOS is increased.

7. The method according to claim 1, wherein proton leak in the mitochondria is decreased.

8. The method according to claim 1, wherein the yield of ATP in the mitochondria is increased.

* * * * *